United States Patent
Schmidt (10) Patent No.: US 11,581,088 B2
(45) Date of Patent: Feb. 14, 2023

(54) METHOD AND DATA PROCESSING SYSTEM FOR PROVIDING RESPIRATORY INFORMATION

(71) Applicant: Siemens Healthcare GmbH, Erlangen (DE)

(72) Inventor: Sebastian Schmidt, Weisendorf (DE)

(73) Assignee: SIEMENS HEALTHCARE GMBH, Erlangen (DE)

(*) Notice: Subject to any disclaimer, the term of this patent is extended or adjusted under 35 U.S.C. 154(b) by 0 days.

(21) Appl. No.: 17/547,345

(22) Filed: Dec. 10, 2021

(65) Prior Publication Data

US 2022/0199232 A1    Jun. 23, 2022

(30) Foreign Application Priority Data

Dec. 23, 2020   (DE) .................... 10 2020 216 557.2

(51) Int. Cl.
| | |
|---|---|
| *G06T 7/00* | (2017.01) |
| *A61B 5/091* | (2006.01) |
| *G16H 30/40* | (2018.01) |
| *G16H 30/20* | (2018.01) |

(52) U.S. Cl.
CPC .......... *G16H 30/40* (2018.01); *G06T 7/0012* (2013.01); *G16H 30/20* (2018.01);
(Continued)

(58) Field of Classification Search
CPC ...... G16H 30/40; G16H 30/20; G06T 7/0012; G06T 2207/10081; G06T 2207/10088;
(Continued)

(56) References Cited

U.S. PATENT DOCUMENTS

| | | |
|---|---|---|
| 2002/0198449 A1 | 12/2002 | Baumgardner et al. |
| 2013/0338489 A1 | 12/2013 | Buxton |
| | (Continued) | |

FOREIGN PATENT DOCUMENTS

| | | |
|---|---|---|
| DE | 102012214786 A1 | 5/2014 |
| DE | 102014009439 A1 | 12/2015 |
| WO | WO 2020231904 A1 | 11/2020 |

OTHER PUBLICATIONS

Bennett et al. "Regional Assessment of Lung Function Using Thin-Plate Splines to Align Structural and Functional Imaging." 37th Annual International Conference of the IEEE Engineering in Medicine and Biology Society, Aug. 25, 2015, pp. 2928-2931 (Year: 2015).*

(Continued)

*Primary Examiner* — Jon Chang
(74) *Attorney, Agent, or Firm* — Harness, Dickey & Pierce, P.L.C.

(57) ABSTRACT

A method is for providing respiratory information. In an embodiment, the method includes receiving imaging data relating to a lung; calculating a perfusion fraction for each respective region of a set of regions of the lung, based on the imaging data; calculating a respective ventilation value for each respective region of the set of regions of the lung based on the imaging data; calculating a weighted average of respective ventilation values across all respective regions of the set of regions of the lung, wherein for each respective region of the set of regions of the lung, the respective ventilation value of the respective region is weighted with the perfusion fraction of the respective region; generating the respiratory information based on the weighted average of the respective ventilation values; and providing the respiratory information.

19 Claims, 2 Drawing Sheets

(52) U.S. Cl.
CPC ........... *G06T 2207/10081* (2013.01); *G06T 2207/10088* (2013.01); *G06T 2207/10108* (2013.01); *G06T 2207/20036* (2013.01); *G06T 2207/30061* (2013.01)

(58) Field of Classification Search
CPC . G06T 2207/10108; G06T 2207/20036; G06T 2207/30061; G06T 7/11; G06T 7/155; A61B 5/091; A61B 5/14542; A61B 6/037; A61B 6/482; A61B 6/5217; A61B 6/582; A61B 6/032; A61B 5/055; A61B 5/702; A61B 5/704; A61B 6/0407; A61B 6/50
See application file for complete search history.

(56) References Cited

U.S. PATENT DOCUMENTS

| | | |
|---|---|---|
| 2015/0216443 A1 | 8/2015 | Baier-Lowenstein et al. |
| 2015/0379706 A1 | 12/2015 | Leonhardt et al. |
| 2016/0367200 A1 | 12/2016 | Voskrebenzev et al. |
| 2017/0027451 A1* | 2/2017 | Suarez Sipmann .. A61B 5/0836 |
| 2017/0325771 A1 | 11/2017 | Tsunomori et al. |

OTHER PUBLICATIONS

Kauczor et al. "Imaging of Pulmonary Pathologies: Focus on Magnetic Resonance Imaging." Proceedings of the American Thoracic Society, vol. 6, 2009, pp. 458-463 (Year: 2009).*
German Office Action and English translation thereof dated Oct. 29, 2021.
German Decision to Grant and English translation thereof dated Mar. 14, 2022.
Wagner, W. L. et al: "Mikrovaskuläre Veränderungen bei COVID-19"; Der Radiologe; Year: 2020, pp.: 934-942, vol. 60.
Chaganti, Shikha et al. "Automated Quantification of CT Patterns Associated with COVID-19 from Chest CT" in: Radiology: Artificial Intelligence, vol. 2, No. 4, 2020, https://arxiv.org/ftp/arxiv/papers/2004/2004.01279.pdf.

* cited by examiner

METHOD AND DATA PROCESSING SYSTEM FOR PROVIDING RESPIRATORY INFORMATION

PRIORITY STATEMENT

The present application hereby claims priority under 35 U.S.C. § 119 to German patent application number DE 102020216557.2 filed Dec. 23, 2020, the entire contents of which are hereby incorporated herein by reference.

FIELD

Example embodiments of the invention generally relate to a method for providing respiratory information, a data processing system, a medical imaging device, a computer program product, and a computer-readable storage medium.

BACKGROUND

Time and again the lung disease COVID-19, which is caused by a novel coronavirus, results in very severe cases and deaths. Unlike other forms of pneumonia, it is noticeable that oxygen saturation or oxygen partial pressure in the blood (pO2) drops very sharply although the lung function (in particular, compliance) is still good and only parts of the lung are affected.

According to currently available information, this is due to the failure of the Euler-Liljestrand mechanism. In healthy people, but also other forms of pneumonia, this reflex regulates the perfusion of parts of the lung which do not participate in ventilation (because an infiltrate is present, that is to say, water is present in the lung). This prevents a large amount of blood from flowing through the pulmonary areas which do not contain any oxygen and then, without absorbing oxygen, reentering the circulatory system of the body.

In the case of COVID-19, this reflex is impaired, resulting in a large amount of blood flowing through the lung and not being oxygenated (shunt effect). The reason for this impairment is not yet clear.

This shunt effect leads to a sharp fall in arterial oxygen saturation and also to great strain on the heart because correspondingly more blood has to be pumped to bring oxygen to the organs. In some cases, this already occurs in patients who only have minor infiltrates.

Patients with pre-existing cardiac conditions are particularly at risk of dying from heart failure although the ventilation parameters are still certainly within an acceptable range.

In contrast, there is the later phase of the disease, when the lung is more evenly affected and the oxygen saturation is rather poor as a result of a lack of diffusion capacity, with the ventilation parameters (e.g. compliance) then also becoming poor.

SUMMARY

The inventors have discovered that it is therefore important to detect and quantify this shunt effect in order to be able to undertake the correct treatment.

At least one embodiment of the invention enables an improved determination of respiratory information.

At least one embodiment of the invention is further directed to a method for providing respiratory information, the method comprising:

receiving imaging data relating to a lung,
calculating a perfusion fraction for each region of a set of regions of the lung based on the imaging data,
calculating a ventilation value for each region of the set of regions of the lung based on the imaging data, calculating a weighted average of the ventilation values across all regions of the set of regions of the lung, wherein for each region of the set of regions of the lung, the ventilation value of this region is weighted with the perfusion fraction of this region,
generating the respiratory information based on the weighted average of the ventilation values, and
providing the respiratory information.

At least one embodiment of the invention is further directed to a data processing system for providing respiratory information, the data processing system comprising:

a receiving component for receiving imaging data relating to a lung,
a calculation component for calculating a perfusion fraction for each region of a set of regions of the lung based on the imaging data,
a calculation component for calculating a ventilation value for each region of the set of regions of the lung based on the imaging data,
a calculation component for calculating a weighted average of the ventilation values across all regions of the set of regions of the lung, wherein for each region of the set of regions of the lung, the ventilation value of this region is weighted with the perfusion fraction of this region,
a generation component for generating the respiratory information based on the weighted average of the ventilation values,
a provision component for providing the respiratory information.

At least one embodiment of the invention is further directed to a medical imaging device comprising the data processing system according to the invention.

At least one embodiment of the invention is further directed to a computer program product with a computer program which can be loaded directly into a storage unit of a data processing system, having program sections to carry out all the steps of a method according to at least one embodiment of the invention when the program sections are carried out by the data processing system.

At least one embodiment of the invention is further directed to a computer-readable storage medium on which program sections readable and executable by a data processing system are stored in order to carry out all the steps of a method of at least one embodiment of the invention when the program sections are executed by the data processing system.

At least one embodiment of the invention is further directed to a method for providing respiratory information, the method comprising:

receiving imaging data relating to a lung;
calculating a perfusion fraction for each respective region of a set of regions of the lung, based on the imaging data;
calculating a respective ventilation value for each respective region of the set of regions of the lung based on the imaging data;
calculating a weighted average of respective ventilation values across all respective regions of the set of regions of the lung, wherein for each respective region of the set of regions of the lung, the respective ventilation value of the respective region is weighted with the perfusion fraction of the respective region;
generating the respiratory information based on the weighted average of the respective ventilation values; and
providing the respiratory information.

At least one embodiment of the invention is further directed to a data processing system for providing respiratory information, the data processing system comprising:

a receiving component to receive imaging data relating to a lung;

a calculation component to calculate a perfusion fraction for each respective region of a set of regions of the lung based on the imaging data;

a calculation component to calculate a respective ventilation value for each respective region of the set of regions of the lung based on the imaging data;

a calculation component to calculate a weighted average of the respective ventilation values across all regions of the set of regions of the lung, wherein for each respective region of the set of regions of the lung, the respective ventilation value of the respective region is weighted with the respective perfusion fraction of the respective region;

a generation component to generate the respiratory information based on the weighted average of the respective ventilation values; and a provision component to provide the respiratory information.

At least one embodiment of the invention is further directed to a medical imaging device, comprising the data processing system of an embodiment.

At least one embodiment of the invention is further directed to a non-transitory computer program product storing a computer program, directly loadable into a storage unit of a data processing system, including program sections to carry out the method of claim 1 when the program sections are executed by the data processing system.

At least one embodiment of the invention is further directed to a non-transitory computer-readable storage medium storing program sections, readable and executable by a data processing system, to carry out the method of claim 1 when the program sections are executed by the data processing system.

At least one embodiment of the invention is further directed to a data processing system for providing respiratory information, the data processing system comprising:

a first interface to receive imaging data relating to a lung; electronic circuitry to calculate a perfusion fraction for each respective region of a set of regions of the lung based on the imaging data, to calculate a respective ventilation value for each respective region of the set of regions of the lung based on the imaging data, to calculate a weighted average of the respective ventilation values across all regions of the set of regions of the lung, wherein for each respective region of the set of regions of the lung, the respective ventilation value of the respective region is weighted with the respective perfusion fraction of the respective region, and to generate the respiratory information based on the weighted average of the respective ventilation values; and a second interface to provide the respiratory information.

At least one embodiment of the invention is further directed to a medical imaging device, comprising the data processing system of an embodiment.

BRIEF DESCRIPTION OF THE DRAWINGS

Hereinafter, the invention is explained based upon example embodiments with reference to the accompanying figures. The illustration in the figures is diagrammatic, greatly simplified and not necessarily true to scale.

The figures show.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one embodiment of the present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc.

Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to a method for providing respiratory information, the method comprising:

receiving imaging data relating to a lung, calculating a perfusion fraction for each region of a set of regions of the lung based on the imaging data, calculating a ventilation value for each region of the set of regions of the lung based on the imaging data, calculating a weighted average of the ventilation values across all regions of the set of regions of the lung, wherein for each region of the set of regions of the lung, the ventilation value of this region is weighted with the perfusion fraction of this region, generating the respiratory information based on the weighted average of the ventilation values, and providing the respiratory information.

In particular, in at least one embodiment, when calculating the weighted average of the ventilation values, the ventilation values weighted with the corresponding perfusion fraction can be added up across all regions.

The respiratory information can in particular comprise and/or be the weighted average of the ventilation values.

The weighted average of the ventilation values across all regions of the set of regions of the lung can in particular be a weighted arithmetic average of the ventilation values across all regions of the set of regions of the lung.

The weighted average of the ventilation values can, for example, be calculated by dividing a sum of products of the perfusion fraction of a region of the set of regions and the ventilation value of the region of the set of regions across all regions of the set of regions of the lung by the sum of the perfusion fractions across all regions of the set of regions.

One embodiment provides that a shunt volume of the lung is calculated based upon the weighted average of the ventilation values, the respiratory information relating to the shunt volume of the lung.

The respiratory information can in particular be generated and/or provided in the form of respiratory information data. The respiratory information can, for example, relate to a pulmonary gas exchange, in particular, pulmonary oxygenation of blood and/or pulmonary ventilation.

Furthermore, it can be provided that the respiratory information relates to oxygen saturation, in particular to an oxygen saturation to be expected at a specific cardiac output.

Furthermore, it can be provided that the respiratory information relates to an oxygen transport capacity, in particular, a current oxygen transport capacity and/or a maximum oxygen transport capacity.

The respiratory information can in particular comprise and/or be the shunt volume of the lung. Furthermore, it can be provided that the respiratory information relates to a result of a comparison of the shunt volume of the lung with a threshold value for the shunt volume of the lung.

The shunt volume of the lung can in particular be a relative shunt volume of the lung. In particular, it can be provided that the sum of the relative shunt volume and the weighted average of the ventilation values is independent of the perfusion fractions and the ventilation values of the set of regions, in particular is equal to a constant, for example equal to one. In the latter case, the relative shunt volume can be calculated, for example, based on the following formula:

$$SV\% = \sum_{n=1}^{x} (V_n\% \cdot P_n)$$

Here, SV % is the relative shunt volume, x the number of regions of the set of regions, Vn % the ventilation value of the nth region of the set of regions and Pn the perfusion fraction of the nth region of the set of regions, wherein the sum of the perfusion fractions Pn across all x regions is equal to one.

One embodiment provides that the set of regions is disjoint in pairs and/or covers the lung.

The set of regions of the lung can in particular, be based on a functional classification and/or a segmentation of the lung. The set of regions of the lung can be based, for example, on a division of the lung into pulmonary lobes, lung segments or into flow areas of vessels.

Furthermore, it can be provided that each region of the set of regions of the lung is a corresponding voxel or a corresponding group of voxels of a medical image data set relating to the lung.

The medical image data set can, for example, be included in the imaging data or generated based upon the imaging data.

A classification data set which relates to the classification of the lung into the regions of the set of regions of the lung can, for example, be included in the imaging data or generated based upon the imaging data.

Furthermore, it can be provided that the lung is a right lobe, that the lung is a left lobe, that the lung includes a right lobe and a left lobe or that the lung includes a right lobe and/or a left lobe.

One embodiment provides that, for each region of the set of regions, the perfusion fraction of this region relates to a fraction of this region in a total perfusion of the lung. In particular, for each region of the set of regions, the perfusion fraction of this region can be a fraction of this region in a total perfusion of the lung.

For example, for each region of the set of regions, the perfusion fraction of this region can be an absolute fraction of this region in a total perfusion of the lung, in particular, such that the sum of the perfusion fractions across all regions is equal to an absolute value of the total perfusion.

For example, for each region of the set of regions, the perfusion fraction of this region can be a relative fraction of this region in a total perfusion of the lung, in particular, such that the sum of the perfusion fractions across all regions is equal to one.

In particular, perfusion data relating to the lung can be received. The perfusion data can be determined, for example, based upon a perfusion assay of the lung. The method for providing the respiratory information can comprise, for example, performing the perfusion assay of the lung. For example, a perfusion fraction can be calculated for each region of the set of regions of the lung based upon the perfusion data and the classification data.

One embodiment provides that for each region of the set of regions, the ventilation value of this region is a quotient of an average gray value of this region and a reference gray value.

In computed tomography, the gray value can be specified as CT density in Hounsfield units. The CT density can be used as a measure of how much water is in the respective region. The higher the water content of a lung part, the less this lung part contributes to the gas exchange as the diffusion path for the oxygen through the water in the alveoli is extended.

The gray value is divided by the reference gray value. With a normal lung density of −900 HU, the relative value of ventilation is equal to 100%. In the case of pure water with 0 HU, no ventilation takes place, and the relative value of ventilation is equal to 0%. This serves as a relative measure for estimating the gas exchange. Analogously, the gas exchange can be estimated from scintigraphy data or from MR data or from a combination thereof.

One embodiment provides that, for each region of the set of regions, the ventilation value of this region relates to a measure of pulmonary gas exchange in this region. In particular, for each region of the set of regions, the ventilation value of this region can be a measure of pulmonary gas exchange in this region.

The pulmonary gas exchange can, for example, be based on a ventilation and/or a diffusion capacity.

In particular, ventilation data relating to the lung can be received. The ventilation data can be determined, for example, based upon a ventilation examination of the lung. The method for providing the respiratory information can comprise, for example, performing the ventilation examination of the lung. For example, a ventilation value can be calculated for each region of the set of regions of the lung based upon the ventilation data and the classification data.

For example, for each region of the set of regions, the ventilation value of that region can be an absolute value of the ventilation of that region. For example, for each region of the set of regions, the ventilation value of that region can be a relative value of the ventilation of that region. For example, the absolute value of the ventilation can be equal to the product of the relative value of the ventilation and a reference ventilation value.

One embodiment provides that calibration data are received which relate to an assignment of values for pulmonary gas exchange to ventilation values, a value for a pulmonary gas exchange in this region being calculated for each region of the set of regions based upon the ventilation value of this region and the calibration data.

The CT density can be used as an indirect measure of the ventilation of a lung region. The ventilation of the lung region can in turn be used as an indirect measure of gas exchange. As these relationships cannot always be mapped linearly, calibration data, for example in the form of a calibration curve, can be used to obtain a measure of the gas exchange from the air content of the regions. The calibration data can in particular be patient-specific.

The calibration data can be generated, in particular, based upon a comparison between examination results for a patient which were determined via different modalities. For example, the calibration data can be generated based upon a comparison of a ventilation scintigraphy in SPECT with a CT examination and/or based upon a comparison of a blood gas analysis with an imaging examination.

Furthermore, it can be provided that the respiratory information is generated based upon the values for pulmonary gas exchange and/or that the shunt volume of the lung is calculated based upon the values for pulmonary gas exchange.

One embodiment provides that the imaging data contains functional imaging data relating to the lung, wherein for each region of the set of regions of the lung, the perfusion fraction of this region is calculated based upon the functional imaging data.

The functional imaging data can contain, for example, perfusion data. The perfusion data can be selected, for example, from a group comprising CT perfusion data, MR perfusion data, SPECT perfusion data, scintigraphy perfusion data and combinations thereof.

One embodiment provides that the imaging data contains morphological imaging data relating to the lung, wherein for each region of the set of regions of the lung, the ventilation value of this region is calculated based upon the morphological imaging data.

In particular, the CT perfusion data and the CT morphology data can be generated based upon the same CT perfusion assay.

One embodiment provides that the imaging data contains spectral CT imaging data relating to the lung, wherein for each region of the set of regions of the lung, the perfusion fraction of this region and the ventilation value of this region are calculated based upon the spectral CT imaging data.

The spectral CT imaging data can be based, for example, on dual energy CT imaging and/or photon counting CT imaging. The spectral CT imaging data can in particular be acquired via a spectral CT scan of the lung.

In particular, it can be provided that the functional imaging data is calculated based upon the spectral CT imaging data and/or that the morphological imaging data is calculated based upon the spectral CT imaging data.

One embodiment provides that the imaging data contains SPECT/CT imaging data relating to the lung, wherein for each region of the set of regions of the lung, the perfusion fraction of this region and the ventilation value of this region are calculated based upon the SPECT/CT imaging data.

In particular, the SPECT/CT imaging data can comprise SPECT perfusion data and CT morphology data.

In particular, it can be provided that the functional imaging data is calculated based upon the SPECT/CT imaging data, for example, based upon the SPECT perfusion data and/or that the morphological imaging data is calculated based upon the SPECT/CT imaging data, for example, based upon the CT morphology data.

In particular, a combination of scintigraphy imaging data and CT imaging data analogous to SPECT/CT imaging data can be used.

V/Q scintigraphy, i.e. the combination of ventilation scintigraphy (with an aerosol or gaseous radiopharmaceutical) and perfusion scintigraphy (with an IV administered radiopharmaceutical) is also suitable for determining ventilation and perfusion of the lung.

One embodiment provides that the imaging data contains ventilation perfusion MR imaging data relating to the lung, wherein for each region of the set of regions of the lung, the perfusion fraction of this region and the ventilation value of this region are calculated based upon the ventilation perfusion MR imaging data.

The ventilation perfusion MR imaging data can be based on Fourier decomposition MR imaging, for example.

In particular, it can be provided that the functional imaging data is calculated based upon the ventilation perfusion MR imaging data and/or that the morphological imaging data is calculated based upon the ventilation perfusion MR imaging data.

One embodiment provides that physiological data relating to the circulatory system and/or ventilation of a patient, in particular, of the patient having the lung, are received, wherein for each region of the set of regions of the lung, the perfusion fraction of this region and/or the ventilation value of this region is further calculated based upon the physiological data.

The physiological data can contain, in particular, circulatory parameters, for example in the form of cardiac output, and/or ventilation parameters, for example in the form of oxygen administration and/or oxygen absorption. In this way, in particular, absolute values for the perfusion fractions and/or ventilation values can be calculated.

At least one embodiment of the invention further relates to a data processing system for providing respiratory information, the data processing system comprising:

a receiving component for receiving imaging data relating to a lung, a calculation component for calculating a perfusion fraction for each region of a set of regions of the lung based on the imaging data, a calculation component for calculating a ventilation value for each region of the set of regions of the lung based on the imaging data, a calculation component for calculating a weighted average of the ventilation values across all regions of the set of regions of the lung, wherein for each region of the set of regions of the lung, the ventilation value of this region is weighted with the perfusion fraction of this region, a generation component for generating the respiratory information based on the weighted average of the ventilation values, a provision component for providing the respiratory information.

The data processing system can be configured in particular for carrying out a method according to an embodiment of the invention.

At least one embodiment of the invention further relates to a medical imaging device comprising the data processing system according to the invention.

The medical imaging device can, for example, be selected from the imaging modalities group including an X-ray device, a C-arm X-ray device, a computed tomography device (CT device), a scintigraphy device, a single photon emission computed tomography device (SPECT device), a positron emission tomography device (PET device), a magnetic resonance tomography device (MR device) and combinations thereof, in particular, a SPECT CT device. The medical imaging device can furthermore comprise a combination of an imaging modality selected, for example, from the imaging modalities group, and an irradiation modality. In this case, the irradiation modality can comprise, for example, an irradiation unit for therapeutic irradiation.

In particular, it can be provided that the imaging data is medical imaging data and/or that the imaging data is acquired via the medical imaging device.

In particular, the method for providing the respiratory information can be a computer-implemented method.

At least one embodiment of the invention further relates to a computer program product with a computer program which can be loaded directly into a storage unit of a data processing system, having program sections to carry out all the steps of a method according to at least one embodiment of the invention when the program sections are carried out by the data processing system.

The computer program product can be, for example, the computer program or, in addition to the computer program, comprise at least one additional component. The at least one additional component of the computer program product can be designed as hardware and/or as software.

The computer program product can, for example, have a storage medium on which at least part of the computer program product is stored, and/or a key for authenticating a user of the computer program product, in particular in the form of a dongle. The computer program product and/or the computer program can comprise, for example, a cloud application program which is designed to distribute program sections of the computer program to various processing units, in particular various computers, of a cloud computing system, each of the processing units being designed to execute one or more program sections of the computer program.

At least one embodiment of the invention further relates to a computer-readable storage medium on which program sections readable and executable by a data processing system are stored in order to carry out all the steps of a method of at least one embodiment of the invention when the program sections are executed by the data processing system.

The computer program product according to one of the embodiments disclosed in this application, and/or the computer program according to one of the embodiments disclosed in this application can be stored on the computer-readable storage medium, for example. The computer-readable storage medium can be, for example, a memory stick, a hard disk, or another data carrier, which can in particular be detachably connected to the data processing system or permanently integrated into the data processing system. The computer-readable storage medium can, for example, form an area of the storage system of the data processing system.

The data processing system can have, for example, one or more components in the form of hardware and/or one or more components in the form of software. The data processing system can, for example, be at least partially formed by a cloud computing system. The data processing system can, for example, be and/or have a cloud computing system, a computer network, a computer, a tablet computer, a smartphone or the like or a combination thereof.

The hardware can, for example, interact with software and/or be configurable via software. The software can be executed, for example, via the hardware. The hardware can be, for example, a storage system, an FPGA system (field-programmable gate array), an ASIC system (application-specific integrated circuit), a microcontroller system, a processor system, and combinations thereof. The processor system can, for example, have a microprocessor and/or a plurality of interacting microprocessors.

The steps of the method can be carried out, for example, in a processor, in particular in the form of calculations.

Data transfer between components of the data processing system can take place, for example, via a suitable data transfer interface. The data transfer interface for data transfer to and/or from a component of the data processing system can be implemented at least partially in the form of software and/or at least partially in the form of hardware. The data transfer interface can be designed, for example, for saving data in and/or for importing data from an area of the storage system, one or more components of the data processing system being able to access this area of the storage system.

Data, in particular the imaging data, the calibration data and/or the physiological data, can be received, for example, by receiving a signal which carries the data and/or by importing the data, in particular from a computer-readable storage medium. Data, in particular the respiratory information, can be provided, for example, by transmitting a signal which carries the data and/or by writing the data into a computer-readable storage medium and/or by displaying the data on a screen.

Within the scope of the invention, features which are described with regard to different embodiments of the invention and/or different claim categories (method, use, apparatus, system, arrangement, etc.) can be combined to form further embodiments of the invention. For example, a claim relating to an apparatus can also be developed having features which are described or claimed in connection with a method, and vice versa. Functional features of a method can be carried out by correspondingly designed components of the subject matter. In addition to the embodiments of the invention expressly described in this application, various further embodiments of the invention are conceivable, which the person skilled in the art can arrive at without departing from the scope of the invention which is specified by the claims.

Figure 1:
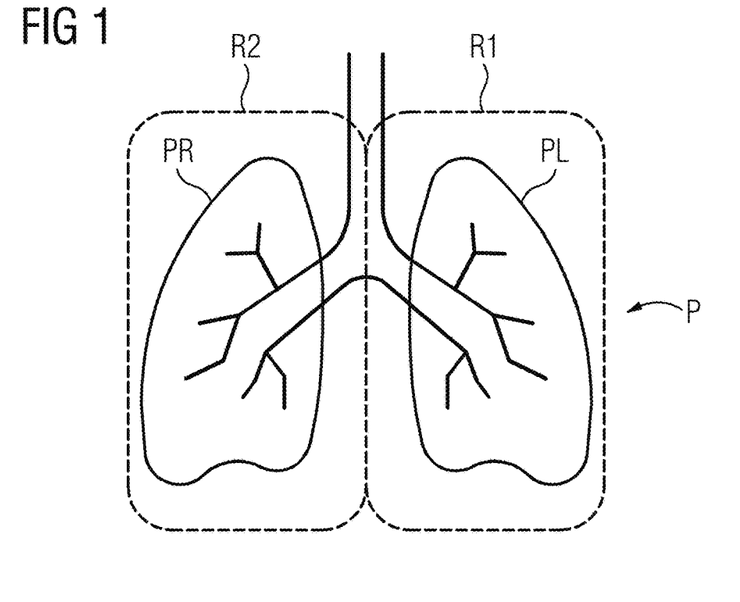
FIG. 1 A lung with a set of regions of the lung.

FIG. 1 shows a lung P with a set of regions R1, R2 of the lung P, the set of regions R1, R2 being disjoint in pairs and covering the lung P.

According to this greatly simplified example, it is provided that the left lobe of the lung PL forms the region R1 and that the right lobe of the lung PR forms the region R2. The perfusion fraction P1 of the region R1 is equal to 40% of the total perfusion of the lung P, P1=0.4. The perfusion fraction P2 of the region R2 is equal to 60% of the total perfusion of the lung P, P2=0.6.

For the ventilation value V1 of the region R1 and the ventilation value V2 of the region R2, for example, V1=20% and V2=80% when the lung P is diseased. In this case, V1=20% results from an average CT density of −180 HU and V2=80% from an average CT density of −720 HU at a reference CT density of −900 HU.

This results in the shunt volume SV % of the lung P when the lung P is diseased, as follows:

$$SV\% = 1-(V1*P1+V2*P2) = 1-(20\%*0.4+80\%*0.6) = 1-(0.08+0.48) = 44\%.$$

The shunt volume is 44%, i.e. only 56% of the blood flowing through the lung P takes part in the gas exchange. Thus, the circulatory load is 1/56%, i.e. approximately twice the normal load.

For the ventilation value V1 of the region R1 and the ventilation value V2 of the region R2, V1=V2=100% when the lung P is healthy.

This results in the shunt volume SV % of the lung P when the lung P is healthy, as follows:

$$SV\% = 1-(100\%*0.4+100\%*0.6) = 0.$$

The shunt volume is thus equal to zero when the lung P is healthy.

Figure 2:
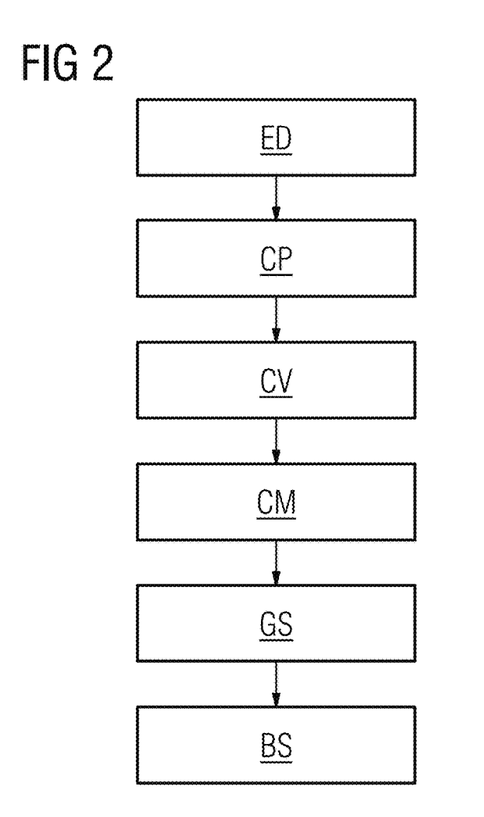
FIG. 2 A flow chart of a method for providing respiratory information.

FIG. 2 shows a flow chart of a method for providing respiratory information, the method comprising Receiving ED of imaging data relating to a lung P, Calculating CP of a perfusion fraction for each region of a set of regions R1, R2 of the lung P based on the imaging data, Calculating CV of a ventilation value for each region of the set of regions R1, R2 of the lung P based on the imaging data, Calculating CM a weighted average of the ventilation values across all regions of the set of regions R1, R2 of the lung P, the ventilation value of this region being weighted with the perfusion fraction of this region for each region of the set of regions R1, R2 of the lung P, Generating GS the respiratory information based on the weighted average of the ventilation values, and Providing BS the respiratory information.

Figure 3:
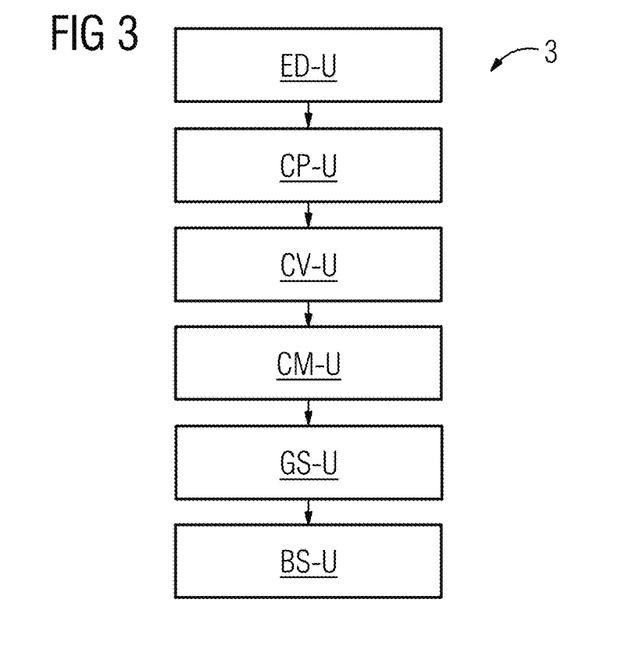
FIG. 3 A data processing system for providing respiratory information.

FIG. 3 shows a data processing system 3 for providing respiratory information, the data processing system 3 comprising:

A receiving component ED-U for receiving ED imaging data relating to a lung P,

A calculation component CP-U for calculating CP of a perfusion fraction for each region of a set of regions R1, R2 of the lung P based on the imaging data, A calculation component CV-U for calculating CV of a ventilation value for each region of the set of regions R1, R2 of the lung P based on the imaging data, A calculation component CM-U for calculating CM a weighted average of the ventilation values across all regions of the set of regions R1, R2 of the lung P, the ventilation value of this region being weighted with the perfusion fraction of this region for each region of the set of regions R1, R2 of the lung P, A generation component GS-U for generating GS the respiratory information based on the weighted average of the ventilation values, and A provision component BS-U for providing BS the respiratory information.

Figure 4:
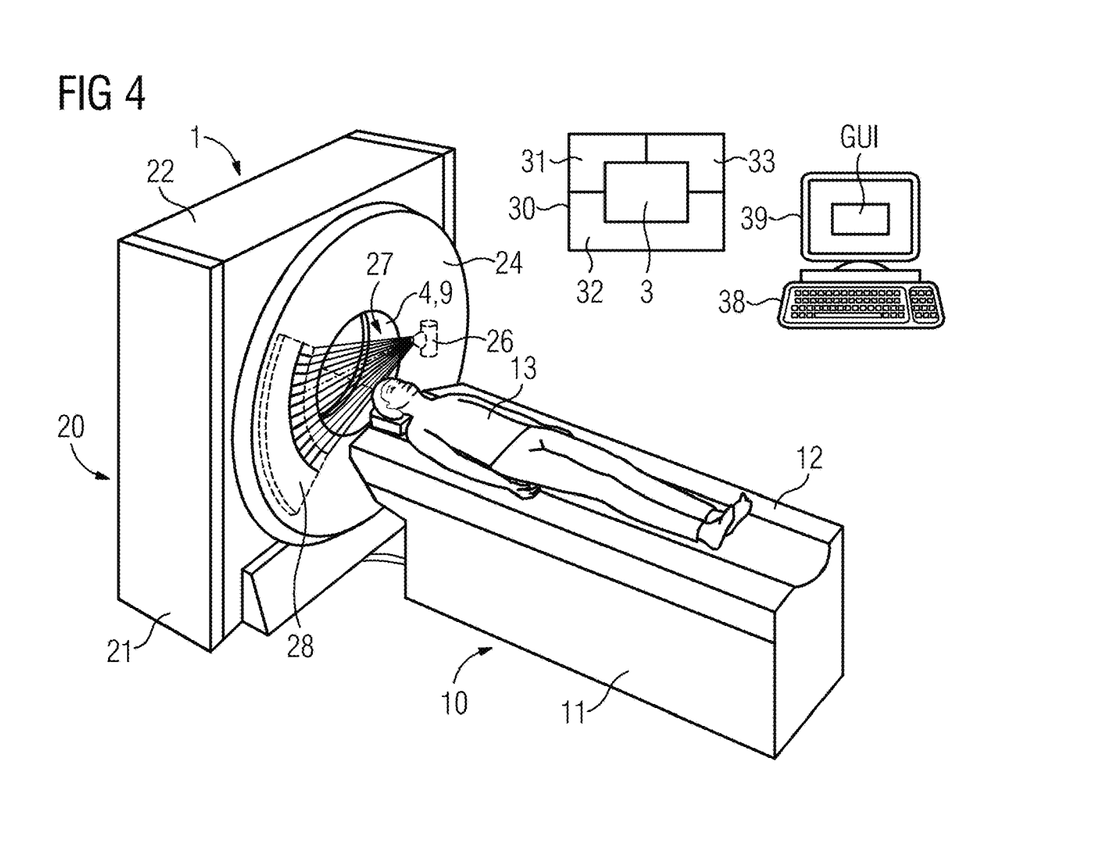
FIG. 4 A medical imaging device.

FIG. 4 shows a medical imaging device 1 comprising the data processing system 3. The medical imaging device 1 is, for example, a CT device, having a gantry 20 with a support frame 21, a tilting frame 22, a rotor 24, a radiation source 26 for emitting X-rays 27 and a radiation detector 28 for detecting the X-rays 27. The gantry 20 has a tunnel-shaped opening 9 in which the acquisition area 4 is located. The medical imaging device 1 also has a patient couch 10 with a bed base 11 and a bed board 12 for receiving the patient 13.

The medical imaging device 1 also has a computer 30 with a memory 31, a data transmission interface 32, a processor 33 and a user interface with an input apparatus 38 and a screen 39, the computer 30 forming the data processing system 3. The respiratory information can be displayed, for example, via the screen 39, in particular, embedded in a graphical user interface GUI.

Of course, the embodiments of the method according to the invention and the imaging apparatus according to the invention described here should be understood as being example. Therefore, individual embodiments may be expanded by features of other embodiments. In particular, the sequence of the method steps of the method according to the invention should be understood as being example. The individual steps can also be performed in a different order or overlap partially or completely in terms of time.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for providing respiratory information, the method comprising:
   receiving imaging data relating to a lung;
   calculating a perfusion fraction for each respective region of a set of regions of the lung, based on the imaging data;
   calculating a respective ventilation value for each respective region of the set of regions of the lung based on the imaging data;
   calculating a weighted average of respective ventilation values across all respective regions of the set of regions of the lung, wherein for each respective region of the set of regions of the lung, the respective ventilation value of the respective region is weighted with the perfusion fraction of the respective region;
   generating the respiratory information based on the weighted average of the respective ventilation values; and
   providing the respiratory information.

2. The method of claim 1,
   wherein a shunt volume of the lung is calculated based upon the weighted average of the respective ventilation values, and
   wherein the respiratory information relates to the shunt volume of the lung.

3. The method of claim 1, wherein the set of regions is disjoint in pairs and covers the lung.

4. The method of claim 1, wherein for each respective region of the set of regions, the respective perfusion fraction of the respective region relates to a fraction of the respective region in a total perfusion of the lung.

5. The method of claim 1, wherein for each respective region of the set of regions, the respective ventilation value of the respective region is a quotient of an average gray value of the respective region and a reference gray value.

6. The method of claim 1, wherein for each respective region of the set of regions, the respective ventilation value of the respective region relates to a measure of pulmonary gas exchange in the respective region.

7. The method of claim 1,
   wherein calibration data are received which relate to an assignment of values for pulmonary gas exchange to ventilation values, and
   wherein for each respective region of the set of regions, a respective value for a pulmonary gas exchange in the respective region based on the ventilation value of the respective region and the calibration data is calculated.

8. The method of claim 1,
   wherein the imaging data includes functional imaging data relating to the lung, and
   wherein for each respective region of the set of regions of the lung, the respective perfusion fraction of the respective region is calculated based upon the functional imaging data.

9. The method of claim 1,
   wherein the imaging data includes morphological imaging data relating to the lung, and
   wherein for each respective region of the set of regions of the lung, the respective ventilation value of the respective region is calculated based upon the morphological imaging data.

10. The method of claim 1,
    wherein the imaging data includes spectral CT imaging data relating to the lung, and
    wherein for each respective region of the set of regions of the lung, the respective perfusion fraction of the respective region and the respective ventilation value of the respective region are calculated based upon the spectral CT imaging data.

11. The method of claim 1,
    wherein the imaging data includes SPECT/CT imaging data relating to the lung, and
    wherein for each respective region of the set of regions of the lung, the respective perfusion fraction of the respective region and the respective ventilation value of the respective region are calculated based upon the SPECT/CT imaging data.

12. The method of claim 1,
    wherein the imaging data includes ventilation-perfusion MR imaging data relating to the lung, and
    wherein for each respective region of the set of regions of the lung, the respective perfusion fraction of the respective region and the respective ventilation value of the respective region based on the ventilation-perfusion MR imaging data are calculated.

13. The method of claim 1,
    wherein physiological data relating to at least one of a circulation and ventilation of a patient are received, and
    wherein for each respective region of the set of regions of the lung, at least one of the respective perfusion fraction of the respective region and the respective ventilation value of the respective region is calculated based upon the physiological data.

14. A data processing system for providing respiratory information, the data processing system comprising:
    a receiving component to receive imaging data relating to a lung;
    a calculation component to calculate a perfusion fraction for each respective region of a set of regions of the lung based on the imaging data;
    a calculation component to calculate a respective ventilation value for each respective region of the set of regions of the lung based on the imaging data;
    a calculation component to calculate a weighted average of the respective ventilation values across all regions of the set of regions of the lung, wherein for each respective region of the set of regions of the lung, the respective ventilation value of the respective region is weighted with the respective perfusion fraction of the respective region;
    a generation component to generate the respiratory information based on the weighted average of the respective ventilation values; and
    a provision component to provide the respiratory information.

15. A medical imaging device, comprising the data processing system of claim 14.

16. A non-transitory computer-readable storage medium storing program sections, readable and executable by the data processing system of claim 14, to carry out a method when the program sections are executed by the data processing system, the method including,
- receiving imaging data relating to the lung;
- calculating the perfusion fraction for each respective region of the set of regions of the lung, based on the imaging data;
- calculating a respective ventilation value for each respective region of the set of regions of the lung based on the imaging data;
- calculating the weighted average of the respective ventilation values across all the respective regions of the set of regions of the lung, wherein for each respective region of the set of regions of the lung, the respective ventilation value of the respective region is weighted with the perfusion fraction of the respective region;
- generating the respiratory information based on the weighted average of the respective ventilation values; and
- providing the respiratory information.

17. The method of claim 2, wherein the set of regions is disjoint in pairs and covers the lung.

18. The method of claim 2, wherein for each respective region of the set of regions, the respective perfusion fraction of the respective region relates to a fraction of the respective region in a total perfusion of the lung.

19. The method of claim 2, wherein for each respective region of the set of regions, the respective ventilation value of the respective region is a quotient of an average gray value of the respective region and a reference gray value.

* * * * *